United States Patent
Koplick et al.

(10) Patent No.: US 6,355,821 B1
(45) Date of Patent: Mar. 12, 2002

(54) PREPARATION OF METAL ALKOXIDES

(75) Inventors: Andrew Joseph Koplick, Ringwood; Susan Marie Jenkins, Balwyn, both of (AU)

(73) Assignee: Sustainable Technologies Australia Limited, Queanbeyan (AU)

( * ) Notice: Subject to any disclaimer, the term of this patent is extended or adjusted under 35 U.S.C. 154(b) by 0 days.

(21) Appl. No.: 09/530,858

(22) PCT Filed: Nov. 6, 1998

(86) PCT No.: PCT/AU98/00921
§ 371 Date: Jul. 5, 2000
§ 102(e) Date: Jul. 5, 2000

(87) PCT Pub. No.: WO99/23865
PCT Pub. Date: May 20, 1999

(30) Foreign Application Priority Data

Nov. 7, 1997 (AU) ............................................... PP0274

(51) Int. Cl.⁷ .......................... C07F 11/00; C07F 19/00; B05D 5/12; C09K 3/00
(52) U.S. Cl. ............................ 556/57; 556/1; 556/42; 556/45; 556/54; 556/76; 556/81; 556/113; 556/130; 556/146; 556/182; 556/400; 423/592; 423/604; 423/606; 423/612; 423/617; 423/618; 427/108; 427/126.3; 252/182.11
(58) Field of Search ............................... 556/1, 42, 45, 556/54, 57, 76, 81, 113, 130, 146, 182, 400; 423/592, 604, 606, 612, 617, 618; 252/182.11; 427/108, 126.3

(56) References Cited

U.S. PATENT DOCUMENTS

| | | | |
|---|---|---|---|
| 3,306,916 A | * 2/1967 | Schenck et al. | 260/429.5 |
| 3,458,306 A | 7/1969 | Lindquist | 75/0.5 |
| 3,931,260 A | 1/1976 | Foley et al. | 260/429.3 |
| 4,347,265 A | 8/1982 | Washo | 427/108 |
| 4,551,358 A | 11/1985 | Lane et al. | 427/126.6 |
| 4,681,959 A | * 7/1987 | Ayen et al. | 556/54 |
| 4,731,461 A | 3/1988 | Greco | 556/81 |
| 4,855,161 A | 8/1989 | Moser et al. | 427/108 |
| 4,996,083 A | 2/1991 | Moser et al. | 427/108 |
| 5,659,417 A | 8/1997 | Van Dine et al. | 359/273 |

FOREIGN PATENT DOCUMENTS

EP 369979 A1 5/1990

OTHER PUBLICATIONS

Zirconium (IV) Tetramer/Octamer Hydrolysis Equilibrium in Aqueous Hydrochloric Acid Solution, Chemical Technology Division of Oak Ridge National Laboratory, Oak Ridge, Tennessee, J. Am. Chem. Soc., 1996.
Metal Alkoxides, Academic Press, London, New York and San Francisco, 1978.
The Crystal Structure of Zirconyl Chloride Octahydrate and Zirconyl Bromide Octahydrate and Zirconyl Bromide Octahydrate, Abraham Clearfield and Philip A. Vaughn Rutgers University, New Brunswick, NJ 1956.
Heterocyclic Compounds, vol. 1, Three–, Four–, Five–, and Six–Membered Monocyclic Compounds Containing One O, N. and S Atom, Robert C. Elderfield, John Wiley & Sons, Inc., New York and Chapman & Hall, Limited London, 1950.

* cited by examiner

Primary Examiner—Porfirio Nazario-Gonzalez
(74) Attorney, Agent, or Firm—Davis & Bujold, P.L.L.C.

(57) ABSTRACT

Methods of forming metal alkoxides and methods of forming precursor solutions of metal alkoxides suitable for the coating of glass in the manufacture of electrochromic devices are disclosed. The method of forming metal alkoxides involves dissolving the metal halide in an anhydrous solvent and reacting it with an alcohol and (together with the addition of the alcohol or subsequently) adding an epoxide, and then evaporating-off the volatile components of the reaction product to leave a solid metal alkoxide that is substantially free of halide. The alkoxide may then be dissolved in a solvent including an alcohol (preferably ethanol) containing a small proportion of water to produce a precursor solution suitable for coating glass, the coating then being hydrolyzed to form a sol-gel and then baked to remove volatile components and to yield a thin layer of metal oxide.

24 Claims, No Drawings

PREPARATION OF METAL ALKOXIDES

TECHNICAL FIELD

This invention primarily relates to metal alkoxides and metal alkoxide solutions suitable for use as precursors in the production of metal oxide coatings on glass and similar substrates, to methods for the preparation of such metal alkoxide precursors and to the coatings and devices employing such coatings. The glass substrates of particular interest are those employed in large-area electrochromic 'smart windows' that require a variety of nanocrystalline metal oxide coatings.

Unless otherwise made clear by the context:

'Metal' refers to any of the conventional metals and also those 'metals' or 'metalloids' of Groups III-A, IV-A and V-A of the Periodic Table of the elements, such as silicon, boron, aluminum, tin, antimony and the like.

'Metal alkoxide' refers to any metal compound derived from an alcohol or alcohol-containing organic moiety wherein the hydroxylic hydrogen of at least one hydroxyl group has been replaced by a metal, and thus includes alkali and alkali earth metal alkoxides.

'Metal halides' includes oxymetal halides.

The metal alkoxides and alkoxide precursor solutions of this invention have particular use in the production of nanocrystalline metal oxide films on large-area glass panels. The films are of high quality, transparent and suitable for use in electrochromic devices. They have valuable application in other areas of industry and technology, such as in catalysts and electronic devices.

BACKGROUND TO THE INVENTION

Metal alkoxides are important in the formation of thin nanocrystalline transparent layers of metal oxides on glass substrates by sol-gel techniques. Typically, the metal alkoxide is applied in a liquid solvent (precursor solution) to a substrate such as glass by dip-coating or spin-coating. The solvent is removed by evaporation and the metal alkoxide is exposed to water vapour to enable hydrolysis and condensation to produce a metal oxide and/or hydroxide sol-gel and alcohol. The coated substrate is then baked at moderate temperatures to remove residual alcohol and form the desired nanocrystalline metal oxide thin layer.

The production of alkoxides from metal halides—especially metal chlorides—for use in electrochromic devices is well known, but the methods are generally tedious and can result in low yields because of the problem posed by the removal of the hydrogen halide by-product. Whereas the reaction of metal chlorides with any of the common alcohols is mildly exothermic and proceeds without difficulty, the standard method of removing by-product HCl (Bradley, D. C.; Mehrotra, R. C.; Gaur, D. P.; Metal Alkoxides, Academic Press, London, 1978) is laborious and involves the use of anhydrous agents in non-aqueous solvents. The HCl by-product is usually allowed to react with a base such as ammonia, alkyl amines, pyridine or sodium alkoxide to produce chloride salts that are insoluble and precipitate from the solvent used. The above textbook reports the use of ammonia for the preparation of alkoxides from the metal halides of Si, Ge, Ti, Zr, Hf, Nb, Ta, Fe, Sb, V, Ce, U and Th. It also reports the use of sodium alkoxide for the preparation of the corresponding metal alkoxides from the metal halides of Ga, In, Si, Ge, Sn, Fe, As, Sb, Bi, Ti, Th, U, Se, Te, W, lanthanides, Ni and Cr.

These methods, however, are cumbersome and suffer from several disadvantages. The fine precipitates (e.g. $NH_4Cl$, $NaCl$) are impractical to filter and the products are obtained only after several prolonged steps of settling, decantation and washing with excess solvent to obtain the maximum yield. Further, in some cases (e.g. Sn, W) the products are often contaminated by the presence of varying amounts of chloride and sodium ions and also $NH_3$ or its derivatives (Bradley, D. C., Caldwell, E. V., and Wardlaw W., Journal of Chemical Society, 1957, 4775; also, vide infra, Example 1). Washing the non-aqueous solution with water to remove chlorides is unacceptable because the metal alkoxides would be rapidly transformed to metal hydroxides and alcohol.

In Japanese patent [Sho 61-36292 (1986)] the following reaction between tungsten hexachloride and n-butanol was described in which part of the HCl was removed under reflux in $CCl_4$ and the remainder with gaseous $NH_3$ as a precipitate of $NH_4Cl$ after the addition of benzene:

$$WCl_6 + ROH + NH_3 \rightarrow O=W(OR)_4 + RCl + nNH_4Cl + (5-n)HCl$$

After three extractions with benzene a yield of 85% of tungsten (VI) oxo-tetra-n-butoxide $[O=W(OBu^n)_4]$ was obtained. The method, however, has the same drawbacks as noted above.

In particular, we have found that, during the preparation of tungsten (VI) oxo-tetra-alkoxide, $[WO(OR)_4]$, from $WOCl_4$, alcohol and ammonia in n-pentane, an insoluble tungsten-containing compound often coprecipitates with ammonium chloride, making the extraction of the product extremely difficult. Reasons for this behaviour are unclear, but insoluble tungsten material could be due to dimer formation or some other incompletely understood interaction of $NH_3$ and/or $NH_4Cl$ with tungsten alkoxide in hydrocarbon solvent. Excess ammonia can be added to dissolve the precipitated tungsten compound, but we have found that the final tungsten oxide obtained from such precursors is unsuitable as a film for electrochromic applications since the reversibility of the colouration-bleaching cycle is inadequate. This is still the case even when no significant amounts of chloride ions and ammonia-derived impurities were detectable in the alkoxide. We believe that the behaviour of $WO_3$ in the film prepared by this route is heavily dependent upon the structure of the precursor tungsten alkoxide, which in turn is influenced by the $NH_3$ concentration during its preparation. Furthermore, we have found that alcoholic solutions of metal alkoxides prepared by the $NH_3$ route are often unstable, resulting in the precipitation of insoluble metal-containing material over time. This means that a single batch of alkoxide produces variable quality coatings.

Similar difficulties with the removal of chloride are encountered in the production of tin alkoxides for use in glass coatings and are addressed in U.S. Pat. No. 4,731,461 (1988). This patent teaches the use of ammonia as described by Bradley et al. as the first step of a two step process in which the product of the first step is treated with a metal amide or a metal alkoxide and additional alcohol. This results in the precipitation of a metal halide salt that can then be removed by filtration. With other metals of interest, particularly tungsten, the two step process taught by U.S. Pat. No. 4,731,461 is not satisfactory. As explained above, the first step is cumbersome, has a poor yield and generates little understood side products that render the resultant alkoxide material unsuitable for electrochromic purposes.

Electrochromic Coatings from Solutions of Metal Chlorides and Alcohols

A number of prior-art patents disclose the production and use of metal alkoxides for use in electrochromic coatings but do not address the problem of chloride removal. For example, in U.S. Pat. No. 4,347,265 (1982) tungsten (VI) chloride ($WCl_6$) is dissolved in an organic solvent such as methanol, isobutanol, ethanol, or acetic anhydride and it is implied that the resultant solution is applied to the substrate without further treatment and then baked to form the desired electrochromic layer. Similarly, U.S. Pat. Nos. 4,996,083 (1991) and 4,855,161 (1989) disclose the preparation of electrochromic coating solutions from anhydrous transition metal halides, preferably chlorides, such as tungsten chloride, and lower carbon, anhydrous alcohols, but no manner of removing contaminating chloride is disclosed. While U.S. Pat. No. 5,659,417 (1997) discloses the use of tungsten and molybdenum alkoxides in alcohol solutions, the method of preparing the alkoxides from metal chlorides, is that of U.S. Pat. No. 4,996,083 outlined above.

Our experience has shown that satisfactory coatings can be made in rare instances by the methods of the just-mentioned patents without removing the chloride impurities. The precursor solutions, however, are unstable and the coatings are prone to discolouration, crazing and, if electrochromic, have poor reversibility and bleaching qualities.

Reactions of Anhydrous Metal Chlorides with Epoxides

The reactions between epoxides and a number of anhydrous metal chlorides have been reported in earlier texts (Heterocyclic Compounds with Three- and Four-membered Rings, Part One, Arnold Weissberger, Editor, Interscience Publishers, 1964, pages 446–451). The mechanisms of reactions leading to the progressive formation of haloalkoxy metal derivatives as well as those leading to the hydrolysed products from these derivatives were discussed. It is known, also, that certain inorganic halides such as $AlCl_3$, $SnCl_4$, $BF_3$ can react vigorously even explosively with epoxides to form tarry or polymerised products. To circumvent these difficulties inert solvent and procedures such as cooling and controlled addition of the epoxides were introduced.

In this context, U.S. Pat. No. b 2,709,174(1955) discloses the careful addition of propylene oxide to anhydrous titanium chloride in aliphatic or aromatic hydrocarbon solvents to avoid side reactions. Nevertheless, the isolated haloalkoxide metal derivatives were reported to be dark brown or black viscous materials probably because of thermal decomposition. U.S. Pat. No. 2,706,181(1955) and U.S. Pat. No. 2,706,189 (1955) disclose the addition of propylene oxide to anhydrous ferric chloride with the preferred solvent being diethyl ether rather than hexane because of the viscous nature of the final product. The materials isolated from this reaction are effective catalysts for the conversion of olefin oxides to solid polymers. Their empirical formula corresponds to $FeX_3(C_3H_6O)_n$ where X is a halogen atom and n has a value from 0.5 to 3.0. The halogen atoms were considered to be part inorganically and part organically bound.

To avoid the disadvantages of readily hydrolysed alkoxy bonds such as those present in $Ti(OR)_4$ where R is an organic group,the authors of U.S. Pat. No. 3,931,260(1976) and U.S. Pat. No. 3,934,068(1976) have disclosed the use of organo-metallic compounds containing more complex beta-haloalkoxy groups with 10 to 25 carbon atoms that were purported to be more resistant to hydrolysis. The compounds were prepared by the reaction of metal halides such as $SiCl_4$ and $TiCl_4$ with one or more higher-molecular-weight epoxides usually in the presence of hydrocarbon solvents. For the purpose of coating glass fiber surfaces to impart abrasion resistance, solutions were made by dissolving the compounds in diacetone alcohol (4-hydroxy-4-methylpentan-2-one) or acetone. Evidently,these polar solvents are convenient for dissolving the higher-molecular-weight organometallic compounds, since the unreactive tertiary alcohol and ketone functional groups would not be able to cleave the metal-oxygen bond formed from primary or secondary haloalkoxy groups. It was asserted, also, that abrasion resistance could be imparted to the coated glass surface by the thermal decomposition of these products to metal oxides, but examples were not given. The metal alkoxides and their derivatives containing up to 18 carbons atoms mentioned in these patents are not suited for producing high-quality metal oxide coatings on glass surfaces, however, because of the likely risk of contamination by carbon from the involatile organic material present and such use was not disclosed.

Since the order of interchangeability of alkoxy groups in alcoholysis reactions (D. C. Bradley, R. C. Mehrotra and D. P. Gaur in Metal Alkoxides,Academic Press, 1978, page 28) is: MeO>EtO>Pr$^i$O>Bu$^t$O the solvolysis of haloalkoxy boron derivatives by methanol was used effectively as an analytical tool by earlier workers (J. D. Edwards, W. Gerrard, and M. F. Lappert, J. Chem. Soc. 348,. 1957).The structure of the borate esters was able to be deduced from a study of the solvolysis products. The borate esters were converted to methyl borate and haloalcohols that then could be isolated and identified. The trischloroalkyl borates $(RO)_3$B were prepared from the direct addition of the neat propene oxide to the boron trichloride at –80° C. and after allowing the mixture to attain room temperature, treated with methanol. No mention of mixed metal alkoxides/haloalkoxides was made.

Methanol, furthermore, would be an unsuitable solvent in the present invention because most metal methoxides are involatile and form insoluble oligomeric species(see Metal Alkoxides, idem, page 46) from which it would be difficult to make dip-coat solutions. Hence, the present disclosure in which alcohols other than methanol exchange with haloalkoxy groups to form mixed metal alkoxy/haloalkoxy compounds is distinct from the prior art.

Reactions of Hydrated Metal Chlorides with Epoxides

The following patents describe the interaction of hydrated metal chlorides and other hydrated metal compounds with epoxides.

U.S. Pat. No. 3,458,306 (1969) discloses the addition of epoxy compounds to hydrated metal chlorides of nickel and aluminum dissolved in an alcohol to produce a metal hydroxide gel. The gel is first heated in an oxidising atmosphere to remove the remaining organics and is then heated in a reducing hydrogen atmosphere to reduce the hydroxide to the metal powder. However, the method cannot produce intermediate alkoxides because of the presence of the water of crystallisation in the hydrated metal chloride. Similarly, U.S. Pat. No. 4,551,358 (1985) discloses a method for the preparation of nickel oxide electrodes by dissolving hydrated cobalt and/or nickel chloride (eg. $NiCl_2.6H_2O$) in an alcohol, optionally with additional water. After applying this solution to a porous nickel substrate and allowing the epoxy compound to contact the impregnated substrate, the volatile by-products are removed by baking. As in the last mentioned patent, the formation of alkoxides for producing metal oxide coatings on glass is prevented by the presence of water in the solution derived from the water of crystallisation and such use was not disclosed.

European Patent No. 369,979 (1989) discloses a way of making fine spherical powders of amorphous hydrated zirconium oxide. In the given example, a process was described in which zirconium oxychloride octahydrate ($ZrOCl_2 \cdot 8H_2O$) was dissolved in 2-methoxyethanol at 60° C. and it was claimed that water was removed as an azeotropic mixture of water and 2-methoxyethanol to produce an essentially anhydrous zirconium salt. It was further claimed that to this zirconium salt was added n-propanol followed by the successive additions of propylene oxide and triethylamine to afford an organic solution of zirconium propoxide. This intermediate zirconium compound was then treated with a mixture of water, oleic acid and n-propanol to effect the hydrolysis and to produce spherical particles of zirconium oxide.

2-Methoxyethanol, a reactive chelating alcohol (Poncelet O., Hubert-Pfalzgraf L. G., Daran J. C. and Astier R., J. Chem. Soc., Chem. Commun., 1846, 1989) was used for dehydration but it was indicated to be an inert solvent merely used to remove water as an azeotropic mixture. To this mixture was then added n-propanol, propylene oxide and triethylamine. The propylene oxide was indicated to act only as an acid scavenger and no explanation for the use of triethylamine was proffered.

Although the reaction details of the dehydration process and structure of the final product remain speculative, the presence of water and a chelating alcohol during the reactive drying process would most likely produce a complex mixture of aggregated zirconium species in which oxo bridges were formed together with chloride and possibly some hydroxy and 2-methoxyethoxy groups remaining associated with the metal ion. Support for this assertion is strengthen by the structure of the initial zirconyl species in question, which is formulated as $[Zr_4(OH)_8 \cdot 16H_2O]^{+8}$. The zirconium atoms are arranged in a square and linked along each edge of the square by a pair of OH groups—one above and the other below the zirconium plane (Clearfield A. and Vaughan P. A., Acta Crystallogr., 1956, 9, 555). There are four additional water molecules bound to each Zr atom and the remaining 12 water molecules and 8 chloride ions form a matrix holding the zirconyl complexes together. Also, the zirconyl complex ion has a propensity to form mixtures of aggregated zirconium species under certain reaction conditions (Singhal A., Toth L. M., Lim J. S. and Affholter K., J. Am. Chem. Soc., 1996, 118, 11529).

Hence, the above-mentioned method, cannot produce an anhydrous metal chloride because of the interaction of a chelating alcohol with a hydrated zirconyl chloride and the disclosure, therefore, is considered to be distinct from that of the present invention. Also, as stated earlier, the presence of ammonia- or alkylamine-derived products gives inferior metal oxide coatings on glass substrates for electrochromic purposes and hence, the above-mentioned process was judged to be unsuitable.

Summary of the Background to the Invention

Since the removal of hydrogen chloride by neutralisation with ammonia during metal alkoxide preparation often gave rise to reaction conditions that led to undesirable side reactions, we have sought to overcome these disadvantages by seeking alternative methods.

We have found that the addition of an epoxide to anhydrous metal halides in the presence of an alcohol results in the removal of the halogen atoms by establishing metal-haloalkoxy bonds as well as haloalcohols. The progressive replacement of halogen atoms by alkoxy and haloalkoxy groups in the metal halides eventually leads to the formation of metal alkoxy/haloalkoxy mixtures. Unlike prior-art methods of allowing epoxides to react directly with anhydrous metal halides,we have found, that if an epoxide is added to an admixture of metal chloride, alcohol and first reaction products,the usually highly exothermic reaction is more easily controlled and thus thermal decomposition is avoided. This procedure ensures, in most cases the efficient substitution of the halide atoms of the metal halides by alkoxy/haloalkoxy groups without tarry products being formed due to the polymerisation of the epoxides. The displaced volatile haloalcohols, excess alcohol and solvent can be readily removed by evaporation from the metal alkoxide product to leave a residue that can be easily re-dissolved in a suitable solvent. This method allows for the effective removal of the halide ions from the metal halide without causing complicated side reactions like those associated with the use of $NH_3$ and alkylamines. The use of such alkoxide precursors results in superior nanocrystalline coatings of metal oxides on glass substrates. We have also found in the case of $WCl_6$ and $VOCl_3$ that alcoholic solutions of their respective metal chloroalkoxides prepared without the removal of the chloroalcohols perform surprisingly well in forming oxide coatings on glass. It appears that any organic chlorine-containing compounds vaporise from the humidified film during drying and/or baking, leaving the properties of the metal oxide coating unaffected.

OBJECTIVES OF THE INVENTION

The general objective of the present invention is to provide methods for the preparation of metal alkoxides that will avoid one or more of the disadvantages associated with the prior art. More particularly, but not essentially, a further objective of the invention is to provide alkoxide coating precursor solutions suitable for use in forming coatings of metal oxides on large-area substrates, such as glass, by the sol-gel technique.

OUTLINE OF THE INVENTION

From one aspect, the present invention involves the reaction of anhydrous metal halides with alcohols so that the presence—or the addition—of an epoxide will result in the formation of a complex mixture of metal alkoxides with alkoxy and haloalkoxy groups attached to the metal. The alcohol can be added to the anhydrous metal halide before the addition of the epoxide or added simultaneously with the epoxide as an admixture. The alcohols can be added in excess or in an amount less than that required stoichiometrically to substitute all chlorine atoms. The molar ratio of alcohol to halogen atom can vary in the range from 10:1 to 0.01:1 but preferably in the range 2:1 to 0.1:1. Any displaced haloalcohols, excess alcohol and inert solvent are readily removed by evaporation or distillation. Exothermic reactions are carried out in the presence of inert hydrocarbon or polar solvents such as pentane, hexane, tetrahydrofuran or diethyl ether to dissipate the heat and lessen thermal decomposition. The preferred organic solvent for most metal chlorides is n-pentane or hexane. With some metal chlorides, for example, $ZnCl_2$, $TaBr_5$, (vide infra, Examples 22, 26) the reaction can be carried out conveniently without solvent and in this case the molar ratio of alcohol to halogen atom can vary in the range 100:1 to 10:1.

From another aspect, the present invention discloses the unexpected result regarding the usefulness of these mixed metal alkoxides as precursors suitable for laying metal-oxide coatings on large-area substrates by the sol-gel techniques. Hydrolyses and condensation reactions of metal alkoxides with alkoxy and/or haloalkoxy groups, free of the influence of alkylamine- or ammonia-derived products, have proven to give superior metal oxide films compared with those prepared by the conventional route. Electrochromic films (eg. $WO_3$) formed from such precursors have been found to have good reversibility and long working lives.

From a further aspect, the present invention discloses the fact that the amount of by-products resulting from adverse reactions such as thermal decomposition or oligomerisation of the epoxides in the presence of metal halides is small, if any under the present conditions Despite the presence of metal alkoxide mixtures and the possibility of by-products being formed, metal oxides films obtained by these procedures are superior in performance to those from prior-art methods.

A typical procedure for forming a transparent metal oxide coating on glass will therefore be: (i) suspend or dissolve the anhydrous halide(s) of the selected metal(s) in an anhydrous organic solvent, (ii) add an alcohol and then an epoxide or a mixture of an alcohol and an epoxide at a rate to control the reaction which forms the metal alkoxide/haloalkoxide mixtures, (iii) remove the volatile components from the reaction product by evaporation or distillation to thereby remove any organic halogen-containing species, (iv) dissolve the residue in an alcohol to form a precursor solution, (v) apply the precursor solution to the glass as thin film, (vi) dry the film releasing any excess alcohol, solvent or residual volatile components, solidifying the coating, (vii) allow the film to adsorb moisture and hydrolyse to form a sol-gel, and (viii) bake the glass and the film to form the desired transparent metal oxide coating.

If the displaced haloalcohols and other volatile components are removed by distillation, the resulting residue is readily re-dissolved in alcohol to give stable precursor solutions from which thin, transparent and substantially defect-free nanocrystalline metal oxide films can be formed on glass substrates by the simple dip-coating, hydrolysis and firing steps known in the art. Preferably, a minor proportion of water is included in the precursor solutions (for example, by inclusion in ethanol) to improve its physical properties.

Epoxides such as ethylene oxide, propylene oxide and butylene oxide can interact initially with either the anhydrous metal halides or with the hydrogen halides generated from the reaction of anhydrous metal halides with alcohol. The addition reaction of hydrogen halides to epoxides results in the formation of halogenated alcohols which in turn can also displace halide anions from the initial metal halide, oxymetal halide or its intermediates to form metal haloalkoxy derivatives and a further molecule of hydrogen halide. Epoxides that react directly with anhydrous metal halides would form halo metal haloalkoxides intermediates. The final distribution of metal alkoxide species, however, would depend upon the reaction rates of the competing processes as shown below. The molar ratio of epoxide to halogen atom can vary in the range from 1:1 to10:1 but preferably at least 2:1.

$$MCl_n + ROH \rightleftharpoons M(OR)Cl_{n-1} + HCl$$

$$MCl_n + \text{epoxide} \longrightarrow M(OR^1)Cl_{n-1}$$

$$\text{Epoxide} + HCl \longrightarrow R^1OH$$

$$M(OR)Cl_{n-1} + R^1OH \rightleftharpoons M(OR)(OR^1)Cl_{n-2} + HCl$$

$$M(OR)Cl_{n-1} + \text{epoxide} \longrightarrow M(OR)(OR^1)Cl_{n-2}$$

$$M(OR)(OR^1)Cl_{n-2} + xROH + yR^1OH \rightleftharpoons M(OR_{1+x}(OR^1)_{1+y} + (n-2)HCl$$

Finally,

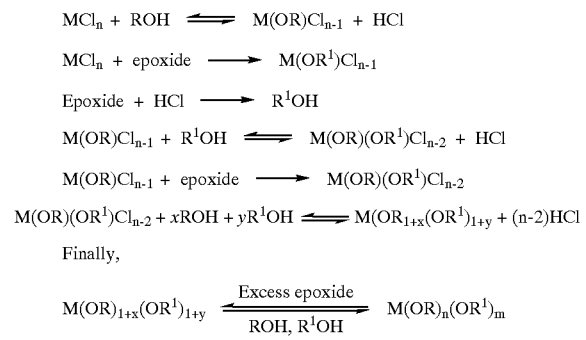

where: 'epoxide' denotes preferably ethylene oxide, propylene oxide or butylene oxide; $0<n<6$; $0 \leq x \leq 4$; $0 \leq y \leq 4$; $x+y \leq 4$; $0<m<6$; $m+n \leq 6$; M is a metal or metal oxide; R is an alkyl group preferably with 2 to 10 carbon atoms and $R^1$ is a chloroalkyl group resulting from the addition of HCl to the corresponding epoxide or from the direct reaction of an epoxide with metal halide or halo metal alkoxide/haloalkoxide intermediates.

As already noted, it is envisaged that the epoxides could react directly with the metal halide in a solvent to displace and capture halide ions in a process forming metal haloalkoxide derivatives. After removing solvent and replacing with alcohol, dip-coat solutions are formed containing metal alkoxide mixtures with alkoxy and haloalkoxy groups and displaced haloalcohols. However, it must be noted that large amounts of haloalcohol fumes given off by films formed from such dip-coat precursor solutions are toxic and would require suitable safety measures during the drying and baking stages. Prior-art methods that have employed sodium alkoxide or ammonia to remove by-product HCl were often contaminated by NaCl or $NH_3$-derived residues, but this problem is avoided by the methods of the present invention.

The method of the invention can be adapted to form alkoxides from a variety of halides, alcohols and epoxy compounds and metal elements in various oxidation states, though halides other than chlorides (eg. fluorides, bromides and iodides) are generally less satisfactory. Metal chlorides which can be used to produce alkoxides by the method of this invention include: $WCl_6$, $WOCl_4$, $WCl_4$, $MoOCl_4$, $VCl_5$, $VOCl_3$, $VCl_3$, $NbCl_5$, $TaCl_5$, $TiCl_4$, $ZrCl_4$, $ZrOCl_2$, $IrCl_3$, $FeCl_2$, $FeCl_3$, $CoCl_2$, $NiCl_2$, $CuCl_2$, $ZnCl_2$, $CdCl_2$, $BCl_3$, $AlCl_3$, $GaCl_3$, $InCl_3$, $TlCl$, $SiCl_4$, $GeCl_4$ $SnCl_4$, $PbCl_4$, $SbCl_5$, $YCl_3$, and lanthanide chlorides. All traces of adventious moisture and chemically combined water should be absent from the metal chlorides. Preferably the metal chlorides are heated under reflux with appropriate reagent such as thionylchloride and the excess is removed by careful distillation at atmospheric pressure and finally under vacuum.

The alcohols can be straight-, branched- or cyclic-alcohols, preferably, containing 2 to 10 carbon atoms, most preferably 2 to 8 carbon atoms. Similarly, a wide variety of epoxides may be used with the lower carbon epoxides such as ethylene oxide, propylene oxide or butylene oxide being preferred. Even polymers or other high molecular weight materials containing epoxide groups, which are insoluble in the reaction medium eg. bisphenol-A-diglycidylether, triglycidylisocyanurate, glycidyl 3-(pentadecadienyl) phenylether, poly[(phenyl glycidylether)-co-formaldehydel] may be used for ease of separation from the other volatile reaction products in certain cases.

DESCRIPTION OF EXAMPLES

Having broadly portrayed the nature of the present invention, a number of particular examples will now be described by way of illustration only.

Example 1 illustrates the prior art method of producing tungsten alkoxide by the conventional $NH_3$ route.

Examples 2, 3 and 4 illustrate methods of producing tungsten alkoxides that conform to the present invention.

Examples 5 and 6 illustrate the preparation of dip-coat tungsten alkoxide precursor solutions from the alkoxide product of Example 1.

Examples 7 to 11 illustrate the preparation of dip-coat tungsten alkoxide precursor solutions from the alkoxide products of Examples 2, 3 and 4.

Examples 12 to 28 illustrate the preparation of metal alkoxides other than tungsten by the methods of the invention.

Examples 29 and 30 illustrate the preparation of metal alkoxides wherein the metal halide is treated initially with epoxide only and the resultant product is then dissolved in solvent alcohol.

PREPARATION OF ALKOXIDES

Example 1 [Prior Art]

To a 1-liter 3-necked flask, with a gas inlet closed with a Teflon tap and also a variable length gas inlet tube secured in position by the rubber seal of an adaptor, is added sublimed $WOCl_4$ (35.6 g, 0.104 mol) in a nitrogen-filled dry box. The flask is then connected to a source of dry nitrogen and $LiAlH_4$-dried n-pentane (ca. 800 cm$^3$) is added by cannula from a storage vessel. The reaction flask is cooled in water/ice bath and dry n-butanol (46.3 g, 58 cm$^3$, 0.625 mol) is added to the mixture by syringe. The solid partially dissolves giving a two-phase liquid system. A reflux condenser is then fitted to the flask with two paraffin oil bubbler vessels at the exit to prevent ingress of moist air and allow the exit of gases.

Dry $NH_3$ gas is distilled from sodium metal and allowed to pass into the reaction mixture. The addition of $NH_3$ is stopped once the gas emerging from the second bubbler reacts alkaline (blue colour) with a piece of damp Universal Indicator paper.

The $NH_4Cl$ precipitate usually begins to settle at this stage, leaving a colourless supernatant liquid containing the alkoxide. After leaving the mixture to settle overnight, the supernatant n-pentane is removed by cannula and filtered into a 1-liter receiver flask. The alkoxide (28.5 g, 58% yield based on $WOCl_4$) is recovered as a white powder after distilling the solvent and excess n-butanol. Two further extractions of the $NH_4Cl$ remaining in the reaction flask with 500 cm$^3$ portions of n-pentane can increase the yield to 80–85%.

A typical elemental analysis of the product is C, 39.0; H, 8.01; N, 0.16; Cl, 0.1%; $C_{16}H_{36}OW$ requires: C, 39.0; H, 7.39%. The detection of small amounts of N in the products of such syntheses has generally been observed. Some samples of alkoxide have been obtained in which the amount of N is over 1% and where the carbon percentages are lower than expected, eg. C, 37.7; H, 7.34; N, 1.38, Cl, 0.12%. Dip-coat solutions prepared from tungsten alkoxide isolated in this manner generally have adequate but variable stability and the electrochromic properties are reasonable but inconsistent.

Very often, however, it has been observed that a tungsten-containing material coprecipitates with the $NH_4Cl$ and causes the whole reaction mixture to thicken.

The insoluble mixture can easily be dispersed by the further addition of excess dry $NH_3$ gas, but dip-coat solutions of tungsten alkoxides from such reaction mixtures produce thin films with very poor and inconsistent electrochromic properties.

Example 2

A 1-liter 3-necked flask was rigorously dried and flushed with dry nitrogen before being charged with $WOCl_4$ (21.0 g, 0.062 mol). After adding n-pentane (500–600 cm$^3$) under a flow of nitrogen, a reflux condenser was fitted. As n-butanol (9.2 g, 11.3 cm$^3$, 0. 124 mol) was allowed to react with $WOCl_4$, acidic fumes of HCl were evolved. The addition of n-butanol was gradual to avoid a violent reaction. To the reaction mixture, 1,2-epoxybutane (22.4 g, 26.9 cm$^3$, 0.31 mol) was slowly added by dropping funnel to give a clear pale yellow pentane solution containing a mixture of tungsten alkoxide species. The n-pentane and n-butanol were dried by molecular sieves (4 Å) at least 24 h before use. After distillation of the solvent and volatile products at atmospheric pressure, a solid tungsten alkoxide was isolated and used directly without further purification in the preparation of a dip-coat solution suitable for forming amorphous tungsten oxide layers on glass.

Example 3

A 10-liter flanged flask with an appropriate head, fitted with an inlet for dry nitrogen, reflux condenser, mechanical stirrer and dropping funnel, was purged of moisture and air. The outlet of the condenser was attached by tube to a paraffin oil bubbler to prevent ingress of moist air and to allow the exit of gases. The whole reactor was immersed in a water bath held at about 5–10° C. The reactor was charged with $WOCl_4$ (697.89 g, 2.043 mol) under a flow of nitrogen and then with 5 liters of n-pentane pre-dried by molecular sieves (4 Å). In a separate flask some n-pentane (about 200 ml), 1,2-epoxypropane (711 g, 857 ml, 12.26 mol) and n-butanol (187 ml, 151 g, 2.043 mol) were mixed and this mixture was added by dropping funnel to the $WOCl_4$/pentane reaction medium over a period of about 1 hour. The rate of addition was adjusted so that the mixture was kept under gentle reflux. When the addition was complete, further n-butanol (757 g, 935 ml, 10.215 mol) was added and the solvent and volatiles were distilled at atmospheric pressure. Excess n-butanol and displaced chloropropanols were removed under reduced pressure to give a white tungsten alkoxide, which was used without purification to prepare a dip-coat solution.

Example 4

To tungsten (VI) chloride (5.79 g, 14.6 mmol) in n-pentane (100cm$^3$) was added a mixture of n-butanol (13.5 cm$^3$, 10.94 g, 0.146 mol) and 1,2-epoxypropane (12.2 cm$^3$, 10.139, 0.175 mol) through a dropping funnel over a period of 15 minutes. The reaction was slow, but eventually a clear, slightly blue-green solution formed.

PREPARATION OF PRECUSOR SOLUTIONS

Example 5

(1 17 g, 144 cm$^3$ 1.579 mol) and then dry ethanol (600 cm$^3$) to form a slurry. After stirring for about 30 minutes, a solution of water (1.53 g, 0.085 cm$^3$) in dry ethanol (95 cm$^3$) was added to the alkoxide slurry upon which the residual tungsten alkoxide dissolved completely. An aliquot of a solution of titanium (IV) isopropoxide in ethanol or isopropanol was added by syringe so that the ratio of W:Ti was 4:1. The solution was slight yellow in colour and after standing overnight was filtered through celite to remove any insoluble particles (see Table 1).

Example 6

Tungsten n-butoxide (20.6 g, 0.042 mol), from Example 1, isolated from an n-pentane solution to which an excess of $NH_3$ had been added was used to make a slurry with dry n-butanol (72 cm$^3$) and ethanol (300 cm$^3$). On stirring for about 30–60 minutes, a solution of water (0.75 g, 0.042 mol) in dry ethanol (45 cm$^3$) was added to the alkoxide solution.

An aliquot of a solution of titanium (IV) isopropoxide in ethanol (5 cm$^3$) was added by syringe so that the ratio of W:Ti was 4:1. The solution was slight yellow in colour and after standing overnight was filtered through celite to remove trace amounts of insoluble material (see Table 1).

Example 7

To the mixed tungsten alkoxide (0.062 mol), from Example 2, was added n-butanol (105 cm$^3$) to form a slurry and then a mixture of water (1.1 g, 0.061 mol) and dry ethanol (408 cm$^3$). After gently heating the solution, the solid tungsten alkoxide quickly dissolved and then Ti(O$^i$Pr)$_4$ was added as a solution in ethanol so that the ratio of W:Ti was 4:1. The solution has remained stable for over 6 months without any precipitation and the electrochromic properties of amorphous WO$_3$ thin films produced from this solution showed excellent colouration-bleaching capabilities (see Table 1).

Example 8

To tungsten alkoxide (23.2 g, 0.068 mol), prepared as in Example 3, was added n-butanol (58 cm$^3$) and then a mixture of water (1.2 g, 0.068 mol) and ethanol (282 cm$^3$). The alcoholic solution of tungsten alkoxide was heated under reflux for about 40 minutes and after standing overnight, was filtered to remove trace amounts of insoluble material. The solution remained stable for several months (see Table 1).

Example 9

To tungsten alkoxide (0.063 mol), prepared as in Example 3, was added a mixture of water (1.13 g, 0.063 mol) and ethanol (313 cm$^3$) and the solution was heated under reflux for 40–60 minutes. Titanium (IV) isopropoxide was added as a solution in ethanol so that the ratio of W:Ti was 4:1 and heating was continued for a further 60 minutes. After heating, the solution appeared slightly opaque and a small amount of insoluble material settled out. After filtering through celite the solution remained stable, free of any insoluble material.

Example 10

To tungsten alkoxide (0.059 mol), prepared as in Example 3, was added n-butanol (50 cm$^3$) and then a mixture of water (1.07 g, 0.059 mol) and ethanol (246 cm$^3$). The solution was heated under reflux for about 40 minutes and then Ti(O$^i$Pr)$_4$ was added as a solution in ethanol so that the ratio of W:Ti was 10:1. Heating was continued for a further 60 minutes. The slight yellow solution was filtered through celite to remove trace amounts of insoluble material.

Example 11

To tungsten alkoxide (0.066 mol), prepared as in Example 3, was added, n-butanol (56 cm$^3$) and then a mixture of water (1.18 g, 0.066 mol) and ethanol (272 cm$^3$). The solution was heated under reflux until the solid alkoxide dissolved and then Ti(O$^i$Pr)$_4$ was added as a solution in ethanol so that the ratio of W:Ti was 10:1. This was followed by the cautious addition of a solution of BuLi in hexane so that the ratio of W:Li was 10:1. The mixture was heated a further 30 minutes and filtered through celite to give a faint yellow solution.

PREPARATION OF METAL ALKOXIDES OTHER THAN TUNGSTEN

In examples 12 to 28 the utility of the method is illustrated. Metal alkoxides of Fe, In, Nb, V, Mo, Ce, Ir, Co, Cu, Zr, Ta, Al, Cd, Sb, Zn, W, and Y have been prepared. Combinations eg. W/Ti, V/Ti, Ce/Ti, In/Sn, Cd/Sn, W/Ir, Sb/Sn, of metal alkoxides can be readily prepared in solutions of ethanol.

Example 12

To anhydrous iron (III) chloride (3.24 g, 0.02 mol) was added dry n-pentane (50 cm$^3$). Then a mixture of n-butanol (11 cm$^3$, 8.9 g, 0.12 mol) and 1,2-epoxypropane (8.5 cm$^3$, 7.0 g, 0.12 mol) was slowly added to the iron chloride. The dark red solution was heated under vacuum to remove all volatiles to give a viscous dark red liquid (ca. 9.7 g) which readily dissolved in ethanol.

Example 13

To anhydrous indium chloride (4.2 g, 0.019 mol) in n-pentane (ca, 50 cm$^3$) was added a mixture of n-butanol (87 cm$^3$, 7.0 g, 0.095 mol) and 1,2-epoxypropane (10 cm$^3$, 8.3 g, 0.143 mol). The resulting mixture was heated under reflux until the indium trichloride dissolved. The volatiles were removed under vacuum to give a colourless viscous liquid (ca. 7.7 g) which could be easily dissolved in ethanol.

Example 14

To anhydrous niobium pentachloride (10.2 g, 0.038 mol) in n-pentane (ca, 100 cm$^3$) was added a portion of n-butanol (4.4 cm$^3$). A vigorous reaction occurred and then a mixture of 1,2-epoxypropane (26.3 cm$^3$, 21.8 g, 0.376 mol) and n-butanol (30 cm$^3$) were cautiously added whilst the reaction flask was externally cooled in an ice-water bath. After the addition was complete, the volatile material was distilled to give a yellow-brown viscous liquid (17.0 g), which could be easily dissolved in ethanol.

Example 15

To VOCl$_3$ (33.66 g, 0.194 mol) was added n-pentane (200 cm$^3$) and the reaction flask was cooled in a water bath. A mixture of isopropanol (15 cm$^3$) and 1,2-epoxypropane (81 cm$^3$, 67.2 g, 1.164 mol) was added through a dropping funnel. As the reaction progressed, the colour changed from brown to light yellow. A further 60 cm$^3$ of isopropanol was added so that the total amount of isopropanol was (75 cm$^3$, 58.5 g, 0.973 mol). After distilling the n-pentane, the mixed vanadium alkoxide was dissolved in a solution of isopropanol to which had been added titanium (IV) isopropoxide so that the ratio of V:Ti was 100:1. The solution was pale yellow in colour and remained stable.

Example 16

To dark green crystals of MoOCl$_4$ (16.24 g, 0.064 mol) was added n-pentane. A mixture of n-butanol (35 cm$^3$, 28.5 g, 0.384 mol) and 1,2-epoxypropane (27 cm$^3$, 22.3 g, 0.384 mol) was slowly added through a dropping funnel. The dark red pentane solution slowly changed to a yellow-brown colour as the molybdenum oxychloride reacted. After distilling the n-pentane and other volatile material, the molybdenum (VI) oxoalkoxide easily dissolved in ethanol to form a stable brown solution. On exposure to air the colour changed to dark blue.

Example 17

To anhydrous cerium (III) chloride (2.03 g, 8.24 mmol) was added dry ethanol (25 cm$^3$) and the mixture was heated to form a creamy suspension. On addition of 1,2- epoxypropane (3.45 cm³, 2.87 g, 49.42 mmol) a greyish-coloured suspension developed. After about 15 minutes of heating, titanium (IV) isopropoxide dissolved in ethanol was added so that the ratio of Ce:Ti was 1:1. The colour of the suspension changed to khaki.

Example 18

To anhydrous grey-coloured iridium (III) chloride (1.04 g, 3.48 mmol) was added n-butanol (1.27 cm³, 1.03 g, 13.90 mmol) and the mixture was heated under reflux until the chloride dissolved to give a brown solution. On cooling, 1,2-epoxypropane (ca.6–8 cm³) was added and the mixture was heated a further 15 minutes. After distilling all volatile material at room temperature and under vacuum, the brown material was redissolved in ethanol.

Example 19

To anhydrous blue-purple cobalt (II) chloride (2.88 g, 22.2 mmol) was added excess n-butanol (ca. 10cm³) and the mixture was heated under reflux until the metal chloride dissolved. On cooling, excess 1,2-epoxypropane (ca. 10 cm³) was added to afford a blue-coloured solution, presumably of cobalt alkoxide.

Example 20

To anhydrous brown-yellow copper (II) chloride (1.61 g, 11.97 mmol) was added n-butanol (20 cm³) to give a brown-green solution after gentle heating. On addition of excess 1,2-epoxypropane (ca. 5–6 cm³) the solution remained brown and stable.

Example 21

To anhydrous zirconium (IV) chloride (4.21 g, 1.81 mol) was added excess n-butanol (ca. 12 cm³) to give a pink-coloured solution. The reaction was exothermic. On addition of excess 1,2-epoxypropane (ca. 8 cm³) a colourless solution developed and remained stable.

Example 22

To anhydrous tantalum (V) bromide (1.87 g, 3.22 mmol) was added excess ethanol (ca. 20 cm³) to give an immediate orange solution. On the addition of excess 1,2-epoxypropane (ca. 2–3 cm³) the solution turned colourless.

Example 23

To anhydrous aluminum (III) chloride (3.44 g, 2.58 mmol) was added 25 cm³ of ethanol to form a solution. On adding excess 1,2-epoxypropane (ca. 10 cm³) an immediate precipitation occurred presumably of a mixed alkoxide.

Example 24

To anhydrous cadmium chloride (1.83 g, 0.01 mol) was added excess dry ethanol (ca. 50 cm³) and the mixture was heated under reflux. To the partially dissolved $CdCl_2$ was added excess 1,2-epoxypropane (ca. 10 cm³) yielding a solution of milky appearance. After the cautious addition of anhydrous $SnCl_4$ (1.2 cm³, 2.6 g, 0.01 mol) dissolved in ethanol (10 cm³) a clear, pale yellow solution resulted. The same procedure may be used with combined cadmium and tin chlorides to produce combined cadmium and tin alkoxides.

Example 25

To anhydrous $SbCl_5$ (22.5 g, 0.075 mol) in n-pentane (ca. 100 cm³) was added a mixture of n-butanol (41.3 cm³, 33.5 g, 0.451 mol) and 1,2-epoxypropane (31.5 cm³, 26.29, 0.451 mol) through a dropping funnel over a period of about 30 minutes. The reaction was exothermic. An oily immiscible product formed initially and then towards the end of the addition a light-brown-coloured solution resulted as the mixed antimony (V) alkoxide was completely soluble in n-pentane. After distilling the solvent and other volatile material, a light brown viscous material remained.

Example 26

To zinc chloride (6.8 g, 0.05 mol) was added dry ethanol (50 cm³) and the mixture was heated under reflux until the zinc chloride partially dissolved to give an opaque solution. An excess of 1,2-epoxypropane (ca. 10 cm³) was added and the reaction mixture was heated for a further 20 minutes under reflux. After distilling the volatile material, a clear viscous liquid (ca. 12 g) remained which was extremely moisture sensitive.

Example 27

To yttrium chloride (0.715 g, 3.66 mmol) was added ethanol (20 cm³) and a clear solution formed. After the addition of excess 1,2-epoxypropane (ca. 3 cm³) the clear solution gelled on standing after about 1.0 h.

Example 28

To vanadium oxychloride (6.09 g, 35.14 mmol) in n-pentane (200 cm³) was added 2,3-epoxypropyl isocyanurate (20.25 g, 70.29 mmol) as a scavenger of HCl. After the cautious addition of isopropanol (32.6 cm³, 25.75 g, 35.14 mmol) the colour of the reaction mixture changed from orange-red to a light yellow. The mixture was filtered to remove the solid isocyanurate and after distillation afforded, presumably, vanadium (v) oxoisopropoxide (4.3 g) in 50% yield.

Example 29

To $WOCl_4$ (6.1 g, 0.018 mol) suspended in about 100 cm³ of hexane was added by dropping funnel excess 1,2-epoxypropane (7 cm³) in hexane (10 cm³). A reaction took place immediately and after heating under reflux, a clear yellow solution resulted in 30 minutes. On cooling a white crystalline material formed which filtered easily and dissolved in n-butanol.

Example 30

A mixture of $WCl_6$ (3.3 g, 0.01 mol) in 100 cm³ of dry n-hexane was cooled to about 5–10° C. in an ice/water bath. Excess 1,2-epoxypropane (5 cm³) in 20 cm³ of hexane was added by dropping funnel to the mixture. Initially, a red colour developed and finally a light yellow hexane solution of tungsten alkoxide formed. On evaporation of the n-hexane, a yellow viscous liquid remained which dissolved freely in n-butanol. The same procedures were conducted with $VOCl_3$ and $FeCl_3$.

TABLE 1

Results showing the Contrast Ratio of Nanocrystalline Electrochromic Tungsten Oxide Films Formed from Alkoxides Prepared by Different Methods

| Example | Method | Reproducibility (a) | Contrast Ratio (b) | Reversibility (c) |
|---------|--------|---------------------|--------------------|--------------------|
| 5 | adequate NH$_3$ (d) | very poor | 3.20 | good |
| 6 | excess NH$_3$ (d) | good | 2.05 | extremely poor |
| 7 | 1,2-epoxypropane | excellent | 4.05 | excellent |
| 8 (e) | 1,2-epoxypropane | excellent | 7.00 | excellent |

Notes
(a) Reproducibility of the method of forming the tungsten alkoxide.
(b) The contrast ratio is the ratio of the light transmittance of the WO$_3$ layer between its bleached and charged state. The thickness and applied charge of 15 mC of the layer was the same in all cases. The wavelength of light employed was 670 Å.
(c) Reversibility refers to the ability of the WO$_3$ films to be cycled between their bleached and coloured states without significant loss of contrast ratio.
(d) See Example 1 for details of experimental procedure.
(e) In contrast to Examples 5 to 7, Example 8 employs a solution of tungsten alkoxide in ethanol with no added titanium (IV) isopropoxide.

What is claimed is:

1. A method of preparing metal alkoxides comprising the steps of allowing an anhydrous metal halide to react with an alcohol and an epoxide under anhydrous conditions to form a reaction product that includes a mixture of metal alkoxides with alkoxy and haloalkoxy moieties bonded to the metal as illustrated in the formula, $$M(OR)_n(OR^1)_m$$

where $0<n<6$; $0<m<6$; $m+n \leq 6$; M is a metal or metal oxide; R is a straight-chain alkyl group preferably with 2 to 10 carbon atoms and $R^1$ is a haloalkyl group resulting either from the addition of HCl to the corresponding epoxide or from the direct reaction of an epoxide with metal halide or halo metal alkoxide/haloalkoxide intermediates.

2. The method according to claim 1, further comprising the steps of first allowing said anhydrous metal halide in an anhydrous solvent and said alcohol to react to form a first reaction product consisting of a mixture of halo metal alkoxides in equilibrium with said metal halide and said alcohol,
then adding said epoxide added to said first reaction product to generate said metal alkoxide mixtures with alkoxy and haloalkoxy moieties bonded to the metal as well as said haloalcohols and said alcohol in equilibrium.

3. The method according to claim 1 further comprising the steps of:
dissolving said anhydrous metal halide in anhydrous alcohol without solvent to produce a first reaction product consisting of a mixture of halo metal alkoxides in equilibrium with said metal halide and said alcohol,
then adding said epoxide to said first reaction product to generate said metal alkoxide mixtures with alkoxy and haloalkoxy moieties bonded to the metal as well as said haloalcohols and said alcohol in equilibrium.

4. The method according to claim 3 further comprising the step of using a molar ratio of said alcohol to said halogen atom of at most 100:1 and at least 10:1.

5. The method according to claim 1 further comprising the steps of:
allowing said anhydrous metal halide and said epoxide to react in the presence of solvent to form halo metal haloalkoxides and/or metal haloalkoxides as first reaction products,
then adding said alcohol to said first reaction product to generate said metal alkoxide mixtures with alkoxy and haloalkoxy moieties bonded to the metal as well as said haloalcohols and said alcohol in equilibrium.

6. The method according to claim 1 further comprising the steps of:
dissolving said anhydrous metal halide in an anhydrous solvent to produce a metal halide solution prior to the addition of said alcohol, and
then adding said alcohol and said epoxide together or in sequence to said metal halide solution.

7. The method according to claim 1 further comprising the steps of:
either adding said alcohol in excess or in an amount less than that required stoichiometrically to substitute the total number of halogen atoms in said metal halide,
adding said epoxide to said first reaction product, in excess of that required by stoichiometry with respect to the number of halogen atoms, to generate said metal alkoxide mixtures with alkoxy and haloalkoxy moieties bonded to the metal with said haloalcohols and alcohol in equilibrium.

8. The method according to claim 7 further comprising the step of using a molar ratio of said alcohol to said halogen atom of at most 10:1 and at least 0.01:1.

9. The method according to claim 7 further comprising the step of using a molar ratio of said alcohol to said halogen atom of at most 2:1 and at least 0.1:1.

10. The method according to claim 7 further comprising the step of using a molar ratio of epoxide to halogen atom of at least 1:1 and at most 10:1.

11. The method according to claim 1 further comprising the step of removing said haloalcohols, said alcohol and any inert solvent by evaporation to leave a mixture of metal alkoxide/haloalkoxide residues substantially free of halide ions and/or halogen atoms bonded to the metal.

12. The method according to claim 1 further comprising the step of:
selecting an anhydrous metal chloride as said anhydrous metal halide;
selecting either n-pentane or hexane as said anhydrous solvent;
selecting chloroalkoxy moieties as said haloalkoxy moieties;
selecting chloroalcohols said haloalcohols;
selecting chloro metal alkoxides as said halo metal alkoxides;
selecting chloride ions as said halide ions;
selecting said chlorine atoms as halogen atoms;
selecting said epoxide from the group comprising ethylene oxide, propylene oxide and butylene oxide as, and
selecting said alcohol from the group comprising branched or straight-chain alcohols with 2–8 carbon atoms.

13. The method according to claim 1 further comprising the step of selecting said anhydrous metal halide as a halide of a metal selected from the group comprising Fe, In, Nb, V, Mo, Ce, Ir, Co, Ni, Cu, Zr, Ti, Ta, B, Al,T Cd, Si, Ge, Pb, Sn, Sb, Zn, W and Y.

14. The method according to claim 13 further comprising the step of selecting tungsten oxytetrachloride as the anhydrous metal chloride and selecting tungsten oxyalkoxide residue said alkoxide residue.

15. The method of preparing a precursor solution for use in forming a transparent metal oxide coating on glass, said method including the step of dissolving the metal alkoxide reaction product of claim 1 in an alcohol, said reaction product comprises metal alkoxides mixtures with alkoxy and chloroalkoxy moieties.

16. A method of forming a precursor solution for use in forming a transparent metal oxide coating on glass, said method comprising the following steps:
   adding n-butanol an d/or ethanol to the metal alkoxide product of the method of any preceding claim to form a mixture, and
   heating said mixture to dissolve said product to produce the precursor solution.

17. A method of preparing a precursor solution for use in forming a transparent metal oxide film on glass in the manufacture of an electrochromic device, said method comprising the following steps:
   dissolving a metal chloride in a solvent comprising a pentane or hexane to form a metal chloride solution under anhydrous conditions;
   adding a straight or branched chain alcohol having 2–8 carbon atoms to the metal chloride solution to generate a first reaction product including chloro metal alkoxides and HCl by-product in equilibrium with the metal chloride under anhydrous conditions;
   allowing HCl to react with an epoxide to form chloroalcohols;
   allowing an epoxide to react with first reaction product to generate said metal alkoxide mixtures with alkoxy and haloalkoxy moieties bonded to the metal with said haloalcohols and alcohol in equilibrium;
   displacing the remaining chlorine atoms bonded to the metal with an alcohol, chloroalcohol or epoxide while under reflux;
   removing said chloroalcohols, excess alcohol and any solvent by evaporation to leave a residue consisting of a metal alkoxide mixture with alkoxy and chloroalkoxy moieties bonded to the metal, and
   dissolving said alkoxide residue in a non-aqueous solvent to form the precursor solution.

18. A method of forming a metal oxide film on glass comprising the steps:
   dissolving at least one anhydrous metal chloride, selected from the chlorides of the metals Fe, In, Nb, V, Mo, Ce, Ir, Co, Ni, Cu, Zr, Ti, Ta, B, Al, Tl, Cd, Si, Ge, Pb, Sn, Sb, Zn, W and Y, in an anhydrous organic solvent, selected from the group of pentanes and hexanes to form a metal chloride solution;
   adding an anhydrous branched-or straight-chain alcohol of 2–8 carbon atoms to said solution to form a first reaction product including chloro metal alkoxides in equilibrium with the dissolved HCl and the said alcohol;
   adding to said first reaction product and by-products an anhydrous epoxide selected from the group ethylene oxide, propylene oxide and butylene oxide to form a final product that includes metal alkoxide mixtures with alkoxy and chloroalkoxy moieties bonded to the metal as well as chloroalcohols;
   separating said chloroalcohols, excess epoxide and solvent from the reaction product by evaporation to produce a residue consisting of said metal alkoxide mixtures;
   dissolving said residue in a non-aqueous solvent and a minor proportion of water to form a precursor solution;
   applying said precursor solution to a glass substrate and allowing it to dry to form a thin alkoxide layer thereon;
   exposing the layer to moisture to hydrolyse said layer and to form a sol-gel layer on said substrate; and
   heating said sol-gel layer to drive off volatile components thereof and to form a layer of metal oxide on the substrate.

19. The method according to claim 17 further comprising the step of using a molar ratio of said alcohol to said halogen atom of at most 10:1 and at least 0.01:1.

20. The method according to claim 17 further comprising the step of using a molar ratio of said alcohol to said halogen atom of at most 2:1 and at least 0.1.

21. The method according to claim 17 further comprising the step of using a molar ratio of epoxide halogen atom of at least 1:1 and at most 10:1.

22. The method of forming a metal oxide film on glass according to claim 18 further comprising the steps of dissolving the said anhydrous metal chlorides without solvent in said alcohol selected from the group comprising branched-or straight-chain alcohol with 2–8 carbon atoms to form first reaction products including chloro metal alkoxides in equilibrium with the dissolved HCl and the said alcohol.

23. The method according to claim 18 further comprising the step of using a molar ratio of said alcohol to said halogen atom of at most 100:1 and at least 10:1 and the molar ratio of epoxide to halogen atom is at least 1:1 and at most 10:1.

24. The method according to claim 1 further comprising the step of employing a mixture of two or more anhydrous metal halides and the precursor solution comprises an admixture or a reaction product of the corresponding metal alkoxides with alkoxy and chloroalkoxy moieties bonded to the respective metals.

* * * * *